United States Patent [19]

Smith et al.

[11] Patent Number: 6,160,191
[45] Date of Patent: Dec. 12, 2000

[54] HYDROCARBON CONVERSION USING LARGE CRYSTAL ZEOLITE CATALYST

[75] Inventors: Robert Scott Smith, Houston, Tex.; Johannes Petrus Verduijn, deceased, late of Leefdaal, Belgium; by Jannetje Maatje van den Berge, executrix, Oostvoorne, Netherlands; Gary David Mohr, League City; Thomas Herman Colle, Houston, both of Tex.

[73] Assignee: Exxon Chemical Patents Inc., Houston, Tex.

[21] Appl. No.: 09/384,942

[22] Filed: Aug. 27, 1999

Related U.S. Application Data

[63] Continuation of application No. 08/953,312, Oct. 17, 1997, abandoned.
[60] Provisional application No. 60/028,717, Oct. 17, 1996.

[51] Int. Cl.$^7$ ............ C07C 5/22; C10G 47/12; C10G 47/00; C10G 11/02
[52] U.S. Cl. .......... 585/475; 208/109; 208/114; 208/118; 208/121; 208/111.01; 208/111.15; 423/702; 423/709; 423/711
[58] Field of Search .......... 423/702, 709, 423/711; 585/475; 208/114, 118, 109, 121, 111.01, 111.15

[56] References Cited

U.S. PATENT DOCUMENTS

| | | | |
|---|---|---|---|
| 3,503,874 | 3/1970 | Michalko | 208/120 |
| 4,375,458 | 3/1983 | Dwyer et al. | 423/329 |
| 4,650,656 | 3/1987 | Dwyer et al. | 423/329 |

FOREIGN PATENT DOCUMENTS

| | | | |
|---|---|---|---|
| 0026963 | 4/1981 | European Pat. Off. | C01B 33/28 |
| 0089825 | 9/1983 | European Pat. Off. | C10G 71/04 |
| 0156594 | 10/1985 | European Pat. Off. | C01B 33/28 |
| 2400485 | 3/1979 | France | C07C 3/50 |
| 777 233 | 6/1957 | United Kingdom . | |
| 831 076 | 3/1960 | United Kingdom . | |
| WO93/08124 | 4/1993 | WIPO | C01B 33/34 |
| WO93/08125 | 4/1993 | WIPO | C01B 33/34 |
| WO93/25475 | 12/1993 | WIPO | C01B 33/34 |

OTHER PUBLICATIONS

Patent Abstracts of Japan, vol. 008, No. 114 (C–225), May 26, 1984 and JP 59026917A (KAO Sekken KK), Feb. 13, 1984.

*Primary Examiner*—Walter D. Griffin
*Assistant Examiner*—Tam M. Nguyen
*Attorney, Agent, or Firm*—Edward F. Sherer

[57] ABSTRACT

A process for converting hydrocarbons by contacting a hydrocarbon feedstream under hydrocarbon conversion conditions with a large crystal zeolite catalyst. The large crystal zeolite of the catalyst used in the hydrocarbon conversion process is made by heating an aqueous zeolite synthesis mixture under agitation to a temperature equal to or less than the effective nucleation temperature of the synthesis mixture. After this step, the aqueous synthesis mixture is heated in the absence of agitation to a temperature equal to or greater than the effective nucleation temperature of the aqueous zeolite synthesis mixture. The process finds particular application in hydrocarbon conversion processes where reduced non-selective acidity is important for reaction selectivity and/or the maintenance of catalyst activity, e.g., toluene disproportionation, dealkylation, alkylation, and transalkylation.

46 Claims, No Drawings

HYDROCARBON CONVERSION USING LARGE CRYSTAL ZEOLITE CATALYST

This application is a continuation of application Ser. No. 08/953,312, filed Oct. 17, 1997, now abandoned which claims priority to U.S. Provisional Patent Application Ser. No. 60/028,717, filed Oct. 17, 1996.

FIELD OF THE INVENTION

This invention relates to the use of large crystal zeolites as a catalyst or catalyst support for hydrocarbon conversion processes.

BACKGROUND OF THE INVENTION

Crystalline microporous molecular sieves, both natural and synthetic, such as zeolites, have been demonstrated to have catalytic properties for various types of hydrocarbon conversion processes. In addition, the crystalline microporous molecular sieves have been used as adsorbents and catalyst carriers for various types of hydrocarbon conversion processes, and other applications. These molecular sieves are ordered, porous, crystalline material having a definite crystalline structure as determined by x-ray diffraction, within which there are a large number of smaller cavities which may be interconnected by a number of still smaller channels or pores. The dimensions of these channels or pores are such as to allow adsorption of molecules with certain dimensions while rejecting those with larger dimensions. The interstitial spaces or channels formed by the crystalline network enable molecular sieves, such as crystalline alumino-silicates, to be used as molecular sieves in separation processes and catalysts and catalyst supports in a wide variety of hydrocarbon conversion processes.

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, titanium oxide, gallium oxide, indium oxide, and mixtures thereof can replace the alumina portion. Accordingly, the terms "zeolite", "zeolites" and "zeolite material", as used herein, shall mean not only molecular sieves containing silicon and, optionally, aluminum atoms in the crystalline lattice structure thereof, but also molecular sieves which contain suitable replacement atoms for such silicon and aluminum, such as silicoaluminophosphates (SAPO) and aluminophosphates (ALPO). The term "aluminosilicate zeolite", as used herein, shall mean zeolites consisting essentially of silicon and aluminum atoms in the crystalline lattice structure thereof.

The catalytic activity of many zeolites relies on their acidity. The substitution of silica with elements such as alumina with a lower valence state creates a positive charge deficiency, which can be compensated by a cation such as a hydrogen ion. The acidity of the zeolite can be on the surface of the zeolite and also within the channels of the zeolite. Within a pore of the zeolite, hydrocarbon conversion reactions such as paraffin isomerization, olefin skeletal or double bond isomerization, disproportionation, alkylation, and transalkylation of aromatics may be governed by constraints imposed by the channel size of the molecular sieve. Reactant selectivity occurs when a fraction of the feedstock is too large to enter the pores to react, while product selectivity occurs when some of the products cannot leave the channels. Product distributions can also be altered by transition state selectivity in which certain reactions can not occur because the reaction transition state is too large to form within the pores of the zeolite. Selectivity can also result from configuration constrains on diffusion where the dimensions of the molecule approach that of the pore system. Non-selective reactions on the surface of the molecular sieve, such as reactions on the surface acid sites of the zeolite, are usually not desirable as such reactions are not subject to the shape selective constraints imposed on those reactions occurring within the channels of the molecular sieve. Thus, resulting products produced by reaction with the surface acid sites of the zeolite are many times undesirable and can also deactivate the catalyst.

Many times it is desirable to carry out hydrocarbon conversion processes using large crystal zeolites. The term "large crystal" is used herein to mean the crystals have a diameter at least of about 2 microns. For example, large crystal zeolites have less specific outer crystal surface area which can reduce during hydrocarbon conversion the amount of reactions which take place on the surface of the zeolite. Furthermore, large crystal zeolites have longer diffusion path lengths which can be used to modify catalytic reactions. For instance, with respect to intermediate pore size zeolites such as a MFI type, increasing crystal size can change the selectivity of the catalyst when it is used in hydrocarbon conversion processes such as the disproportionation of toluene to paraxylene and the alkylation of aromatics. In the disproportionation of toluene to paraxylene, increasing the size of the zeolite crystal to lengthen the diffusion path increases paraxylene selectivity. The selectivity occurs because an increase in the diffusion constraints is imposed on the bulkier, slower diffusing o- and m-xylene isomers which reduces the production of these isomers and increases the yield of paraxylene isomer.

SUMMARY OF THE INVENTION

In accordance with the present invention, there is provided a process for converting a hydrocarbon feedstream under hydrocarbon conversion conditions with a zeolite catalyst comprising large crystal zeolites. The large crystal zeolites used in the process of the present invention are made by a process which comprises the step of heating an aqueous zeolite synthesis mixture under agitation to a temperature equal to or less than the effective nucleation temperature of the synthesis mixture. After this step, the aqueous synthesis mixture is heated in the absence of agitation to a temperature equal to or greater than the effective nucleation temperature of the aqueous zeolite synthesis mixture. As used in the specification and claims, the term "effective nucleation temperature" means the temperature at which continued stirring of the heated zeolite synthesis mixture would result in significant decrease of the mass mean crystal diameter of the product zeolite crystals, e.g., a reduction of the mass mean crystal diameter of the product crystals of 15 percent or greater. Preferably, the selected temperature to which the synthesis mixture is heated with stirring will result in a reduction of the mass mean crystal diameter of the product zeolite crystals of less than 10 percent, more preferably less than 5 percent.

The process of the present invention has application in hydrocarbon conversion processes and finds particular application hydrocarbon conversion processes where reduced non-selective acidity is important for reaction selectivity and/or the maintenance of catalyst activity, such as alkylation, dealkylation, disproportionation, and transalkylation reactions.

DETAILED DESCRIPTION OF THE INVENTION

Zeolites useful in the process of the present invention include any of the naturally occurring or synthetic crystalline zeolites. Examples of these zeolites include large pore zeolites, medium pore zeolites, and small pore zeolites. These zeolites are described in "Atlas of Zeolite Structure Types", eds. W. H. Meier, D. H. Olson and Ch. Baerlocher, Elsevier, Fourth Edition, 1996, which is hereby incorporated by reference. A large pore zeolite generally has a pore size of at least about 7 Å and includes LTL, VFI, MAZ, MEI, FAU, EMT, OFF, *BEA, and MOR structure type zeolites (IUPAC Commission of Zeolite Nomenclature). Examples of large pore zeolites, which correspond to a structure type listed above, include mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size zeolite generally has a pore size from about 5 Å to about 7 Å and includes, for example, MFI, MEL, MTW, EUO, MTT, HEU, FER, MFS, and TON structure type zeolites (IUPAC Commission of Zeolite Nomenclature). Examples of intermediate pore size zeolites, which correspond to a structure type listed above, include ZSM-5, ZSM-12, ZSM-22, ZSM-23, ZSM-34, ZSM-35, ZSM-38, ZSM-48, ZSM-50, ZSM-57, silicalite, and silicalite 2. A small pore size zeolite has a pore size from about 3 Å to about 5.0 Å and includes, for example, CHA, ERI, KFI, LEV, and LTA structure type zeolites IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, erionite, chabazite, zeolite T, gmelinite, ALPO-17, and clinoptilolite.

In general, the chemical formula of anhydrous crystalline metallosilicate can be expressed in terms of moles as represented by the formula: $M_{2/n}O:W_2O_3:ZSiO_2$, wherein M is selected from the group consisting of hydrogen, hydrogen precursors, monovalent, divalent and trivalent cations and mixtures thereof; n is the valence of the cation and Z is a number of at least 2, preferably at least 3, said value being dependent upon the particular type of zeolite, and W is a metal in the anionic framework structure of the zeolite such as aluminum, gallium, boron, or iron.

When the zeolite has an intermediate pore size, the zeolite preferably comprises a composition having the following molar relationship:

$$X_2O_3:(n)YO_2,$$

wherein X is a trivalent element, such as aluminum, gallium, zinc, iron, and/or boron, Y is a tetravalent element such as silicon, tin, and/or germanium; and n has a value greater than 10, usually from about 20 to less than 20,000, more usually from 50 to 2,000, said value being dependent upon the particular type of zeolite and the trivalent element present in the zeolite.

As known to persons skilled in the art, the acidity of a zeolite can be reduced using many techniques such as by dealumination and steaming. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina and silica to gallia disclosed herein shall include not only zeolites having the disclosed mole ratios, but shall also include zeolites not having the disclosed mole ratios but having equivalent catalytic activity.

When the zeolite is a gallium silicate intermediate pore size zeolite, the zeolite preferably comprises a composition having the following molar relationship:

$$Ga_2O_3:ySiO_2$$

wherein y is between about 20 and about 500, typically from 20 to 200. The zeolite framework may contain only gallium and silicon atoms or may also contain a combination of gallium, aluminum, and silicon.

When the zeolite used in the zeolite catalyst is an aluminosilicate zeolite, the silica to alumina mole ratio will usually depend upon the structure type of the zeolite and the particular hydrocarbon process in which the catalyst system is utilized and is therefore not limited to any particular ratio. Generally, however, and depending on the structure type of the zeolite, the zeolite will have a silica to alumina mole ratio of at least 2:1 and in some instances from 4:1 to about 7:1. For a number of zeolites, especially intermediate pore size zeolites, the silica to alumina mole ratio will be in the range of from about 10:1 to about 1,000:1. When the catalyst is utilized in acid catalyzed reactions such as cracking, the manufacture of paraxylene and benzene by the disproportionation of toluene, the alkylation of benzene or the like, the zeolite will be acidic and will preferably, when it is an intermediate pore size zeolite, have higher silica to alumina mole ratios, e.g., 20:1 to about 200:1.

The structure type of the zeolite will depend on the particular hydrocarbon process in which the zeolite catalyst system is utilized. For instance, if the catalyst system is used for the reforming of naphtha to aromatics, the zeolite type will preferably be LTL (example Zeolite L) and have a silica to alumina ratio from 4:1 to about 7:1. If the catalyst system is be used for xylene isomerization or the manufacture of paraxylene and benzene by the disproportionation of toluene, the zeolite will preferably be an intermediate pore size zeolite, such as a MFI structure type (example ZSM-5). If the zeolite catalyst system is to be used for cracking paraffins, the preferred pore size and structure type will depend on the size of the molecules to be cracked and the desired product. The selection of the structure type for hydrocarbon conversion processes is known to persons skilled in the art.

The large crystal zeolite used in the process of the present invention will preferably have a mass mean diameter of from about 3 to about 10 microns and, more preferably, will have a mass mean diameter of from about 3 to about 6 microns. When the zeolite is an intermediate pore size zeolite such as an MFI structure type, preferably the crystals will have no more than about 5% on a mass basis of zeolite crystals less than 1 micron diameter.

The large zeolite crystals used in the process of the present invention are preferably made by a process which comprises the following steps:

(a) forming an aqueous reaction mixture containing sources of a trivalent metal oxide such as alumina or gallia, silica, alkali metal cations, optionally from 0 to about 10 weight percent seed crystals based on the weight of the reaction mixture and, optionally a directing agent;

(b) heating the aqueous reaction mixture under agitation and for sufficient time to a temperature no greater than the effective nucleation temperature of the aqueous reaction mixture to effect heat transfer to the aqueous reaction mixture to achieve a more uniform temperature in the aqueous reaction mixture; and (c) heating the aqueous reaction mixture of step (b) in the absence of any further agitation to a temperature equal to or greater than the effective nucleation temperature of the aqueous reaction mixture and for sufficient time to result in the production of large zeolite crystals.

Procedures to determine zeolite crystal size are known to persons skilled in the art. For instance, crystal size may be determined directly by taking a suitable scanning electron microscope (SEM) picture of a representative sample of the zeolite crystals.

The sources of the various elements of the zeolite may be any of those in commercial use or described in the literature, as may the preparation of the synthesis mixture.

For example, the source of silicon may be a silicate, e.g., an alkali metal silicate, a tetraalkyl orthosilicate, a precipitated silica, or an aqueous colloidal suspension of silica, for example one sold by E.I. du Pont de Nemours under the trade name Ludox.

When the zeolite as an aluminosilicate zeolite, the source of aluminum is preferably hydrated alumina. Other aluminum sources include, for example, alumina metal, a water-soluble aluminum salt, e.g., aluminum sulphate, or an alkoxide, e.g., aluminum isopropoxide.

Optionally a directing agent, such as an organic or inorganic compound containing nitrogen, oxygen, sulfur, or phosphorous may be introduced into the synthesis mixture in either powder form or as an aqueous solution which is preferred. The cation may also be introduced in the form of a mixture of hydroxide and salt, e.g., a halide. The agent used will depend on the zeolite prepared by the process.

The order of mixing of the ingredients is not essential and will depend largely on the zeolite being prepared. For instance, the synthesis mixture can be prepared by dissolving the aluminum source in an aqueous caustic solution and then adding this to a mixture of a silica source in water.

Equipment used to prepare the zeolite crystals of the present invention are known to persons skilled in the art. For example, zeolites can be commercially prepared by using large autoclaves which have sufficient agitation to homogenize the zeolite reaction mixture during heat up until the effective nucleation temperature of the mixture is achieved. In general, stirring can be continued to any temperature below the effective nucleation temperature with little or no impact on product zeolite crystal size. However, if stirring is continued above the effective nucleation temperature, the product zeolite crystal size will decrease. Stirring to progressively higher temperatures above the effective nucleation temperature, or prolonged stirring at a temperature above the effective nucleation temperature, will lead to progressively larger decreases in size of product zeolite crystal. The effective nucleation temperature of the synthesis mixture will depend on the composition of the synthesis mixture which in turn will be governed by the zeolite being prepared. With respect to the preparation of an MFI type zeolite (e.g., ZSM-5), the synthesis mixture is preferably heated with agitation provided by a mixing device which will move the mixture in a turbulent fashion such as occurs with a pitch blade turbine mixer. Other means of introducing agitation known to one skilled in the art can be employed, such as pumping the synthesis mixture from one part of the autoclave to another. The purpose of the agitation is to assist heat transfer to the synthesis mixture in a uniform manner, but the degree of agitation should be low enough to minimize shear-induced seed formation in the synthesis mixture. When a turbine mixer is employed, the degree of agitation can be measured as the speed at which the blade tip moves through the synthesis mixture (tip speed). Preferably the tip speed should be less than about 5 meters per second (M/s) and more preferably less than about 3.5 M/s. The tip speed of the mixer can also be varied depending on the temperature distribution of the synthesis mixture and changes in mixture viscosity during heat up. Preferably a constant tip speed of about 1–2.0 M/s is used until a temperature from about 100 to about 120° C. is reached, and then the tip speed is increased gradually as heat up continues until the nucleation temperature is reached. Most preferably the maximum tip speed is about 2–5 M/s at a temperature of about 130 to about 150° C. and most preferably from about 2 to about 3.5 M/s at a temperature from about 140 to about 150° C. The time required for heat up of the reaction mixture should be as fast as practical to minimize the amount of time the synthesis mixture is agitated to reduce shear induced seeding. The time during which stirring occurs at temperatures above 130° C. is preferably less than about 6 hours and more preferably less than 3 hours. After the synthesis mixture reaches the effective nucleation temperature, the agitation is stopped. Heating of the reaction mixture can be allowed to occur after the stop of agitation with no undue effect to product quality. The temperature can also be maintained at the temperature reached when agitation was stopped. The synthesis mixture can also be allowed to cool after the agitation is stopped, but for MFI structure type zeolites, preferably the temperature is maintained between about 130° C. and about 150° C. The effective nucleation temperature can be confirmed by procedures known in the art such as by x-ray detection of crystal presence greater than any seed level. Changes in synthesis mixture viscosity during heat up can also be used to determined the onset of crystallization. The effective nucleation temperature will be a function of the type of zeolite being prepared and may often be expressed as a temperature range rather than a single sharply defined temperature, but will generally be between about 120° C. and about 150° C. for MFI type zeolites. For ZSM-5, the effective nucleation temperature will usually be in the range of from about 130 to about 150° C. The time required for the crystallization under static conditions will vary, but is preferably between about 4 and about 48 hours. More preferably the crystallization time is between about 12 and about 36 hours. The crystallization time can be established by methods known in the art such as by sampling the reaction mixture at various times and determining the yield and x-ray crystallinity of precipitated solid. The control of product crystallite size can be facilitated if the reaction mixture additionally comprises from about 0.05 ppm to about 10.0 percent seeds of zeolite based on the weight the synthesis mixture. The use of seeds to control zeolite crystallite size is disclosed in U.S. Pat. No. 5,672,331, which is hereby incorporated by reference. Seeds can be added to control the mass mean crystallite diameter. Even though the seed level can give crystal diameters within certain particular ranges, large crystals may not be achievable by reducing seeding level without employing the present invention. Stirring can affect the amount of seeds that are used when done above the effective nucleation temperature and preferably the seed level is from about 0.05 ppm to about 0.1 wt. % and more preferably from about 0.0001 to about 0.05 wt. %.

When the catalyst comprises a MFI type aluminosilicate large crystal zeolite, the zeolite is preferably prepared from a reaction mixture having a composition expressed in terms of mole ratios of oxides, as follows:

| Reactants | Preferred | More Preferred |
|---|---|---|
| $SiO_2/Al_2O_3$ | >50 | 70 to 20,000 |
| $H_2O/SiO_2$ | 10 to 100 | 15 to 50 |
| $OH/SiO_2$ | 0.01 to 0.5 | 0.01 to 0.2 |
| $R/SiO_2$ | 0.001 to 2.0 | 0.05 to 1.0 |

[1]R is directing agent selected from a group consisting of nitrogen, sulfur, oxygen, and phosphorous containing inorganic and organic compounds.

Upon completion of crystallization of the zeolite from the reaction mixture, the product crystals are separated, as by cooling and filtering, and are water washed and dried at a temperature of typically from about 250 to about 250° C., and more preferably from 80° C. to about 120° C.

In the case of many catalysts, it is desirable that crystalline zeolites be incorporated with binder material resistant to the temperature and other conditions employed in organic conversion processes. Such binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid, treatment or chemical modification.

In addition to the foregoing materials, the zeolites as prepared herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The zeolite may also be composited with zeolitic material such as the zeolitic materials which are disclosed in PCT Publication 96/16004, which is hereby incorporated by reference.

When zeolitic materials are used to bind the large crystal zeolite, the structure type of the zeolitic materials can include large pore, intermediate pore and large pore zeolites and the structure type of the zeolite binder can be the same or can be different from the large crystal zeolite.

The zeolite catalyst may be further ion exchanged after calcination to remove organic template as is known in the art either to replace at least in part the original alkali metal present in the zeolite with a different cation, e.g., a Group 1B to VIII Periodic Table metal such as nickel, copper, zinc, palladium, platinum, calcium or rare earth metal, or to provide a more acidic form of the zeolite by exchange of alkali metal with intermediate ammonium, followed by calcination of the ammonium form to provide the acidic hydrogen form. The acidic form may be readily prepared by ion exchange using a suitable acidic reagent such as ammonium nitrate. The zeolite catalyst may then be calcined at a temperature of 400–550° C. for a period of 10–45 hours to remove ammonia and create the hydrogen form. Ion exchange is preferably conducted after formation of zeolite catalyst. Particularly preferred cations are those which render the material catalytically active, especially for certain hydrocarbon conversion reactions. These include hydrogen, rare earth metals, and metals of Groups IIA, IIIA, IVA, IB, IIB, IIIB, IVB, and VIII of the Periodic Table of the Elements. Preferred metals include Group VIII metals (i.e., Pt. Pd, Ir, Rh, Os, Ru, Ni, Co, and Fe), Group IVA metals (i.e., Sn and Pb), Group VB metals (i.e., Sb and Bi), and Group VIIB metals (i.e., Mn, Tc, and Re). Noble metals (i.e., Pt, Pd, Ir, Rh, Os, and Ru) are sometimes more preferred.

The hydrocarbon conversion processes are used for processing hydrocarbon feedstocks. Hydrocarbon feedstocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed can also have high or low nitrogen or sulfur impurities.

The conversion of hydrocarbon feeds can take place in any convenient mode, for example, in fluidized bed, moving bed, or fixed bed reactors depending on the types of process desired.

Examples of hydrocarbon compound conversion processes that find application in the process of the present invention include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst, feed rate) from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 hr-1.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 100 hr-1 and an aromatic hydrocarbon/polyalkylaromatic hydrocarbon mole ratio of from about 0.5/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 hr-1 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 hr$^{-1}$ to about 100 hr$^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 hr$^{-1}$ to about 2000 hr$^{-1}$ and an aromatic hydrocarbon/olefin mole ratio of from about 1/1 to about 20/1. The resulting products from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 hr$^{-1}$ to about 50 hr$^{-1}$;

(I) The hydrocracking of heavy petroleum feedstocks, cyclic stocks, and other hydrocrack charge stocks. The zeolite catalyst system will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 to about 800 psig, a WHSV-olefin from about 0.4 hr$^{-1}$ to about 0.8 hr$^{-1}$, a WHSV-reformate of from about 1 hr$^{-1}$ to about 2 hr$^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 160° C. to about 260° C. and pressures from about 350 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 hr$^{-1}$ to about 10 hr$^{-1}$.

(M) The conversion of light paraffins to olefins and/or aromatics. Typical reaction conditions include temperatures from about 425° C. to about 760° C. and pressures from about 10 to about 2000 psig. Processes for preparing aromatic compounds from light paraffins are described in U.S. Pat. No. 5,258,563, which is hereby incorporated by reference.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals In a first stage, the zeolite catalyst comprising one or more catalytically active substances, e.g., a Group VIII metal, and the effluent from the first stage would be reacted in a second stage using a second zeolite catalyst, e.g., zeolite Beta, comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the zeolite catalyst comprising a hydrogenation component and a zeolite such as zeolite Beta. Typical reaction conditions include temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to produce mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 hr$^{-1}$ to about 200 hr$^{-1}$ and an alcohol to olefin molar feed ratio from about 0.1/1 to about 5/1.

(R) The disproportionation of aromatics, e.g., the disproportionation of toluene to make benzene and, paraxylene. Typical reaction conditions include a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g., $C_6$–$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) The adsorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a zeolite catalyst at a temperature in the range of from about 250° C. to about 800°, a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, the catalytic conversion conditions include a temperature of from about 100° C. to about 760° C., a pressure of from about 0.1 atmosphere (bar) to about 200 atmospheres (bar), a weight hourly space velocity of from about 0.08 $hr^{-1}$ to about 2,000 $hr^{-1}$.

The process of the present invention finds application in the vapor phase disproportionation of toluene. Such vapor phase disproportionation comprises contacting toluene under disproportionation conditions with the zeolite catalyst to yield a product mixture which comprises a mixture of unreacted (unconverted) toluene and benzene and xylene. In the more preferred embodiment, the catalyst is first selectivated prior to use in the disproportionation process. Processes for selectivating the catalyst are known to persons skilled in the art. For instance, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst.

Selectivation of the catalyst can also be accomplished by treating the catalyst with a selectivation agent such as an organosilicon compound. The silica compounds may comprise polysiloxane including silicone and siloxanes, and a silane including disilanes and alkoxysilanes.

Silicone compounds that find particular application can be represented by the formula:

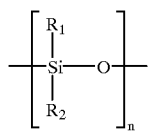

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methyl hydrogensilicone, ethylhydrogensilicone, phenylhydrogensilicone, methylethylsilicone, phenylethylsilicone, diphenylsilicone, methyltri fluoropropylsilicone, ethyltrifluoropropylsilicone, tetrachlorophenyl methyl silicone, tetrachlorophenylethyl silicone, tetrachloro phenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethyl cyclopentasiloxane, hexamethyldisiloxane, octamethyltrisiloxane, decamethyltetrasiloxane, hexaethylcyclotrisiloxane, octaethylcyclo tetrasiloxane, hexaphenylcyclotrisiloxane and octaphenylcyclo tetrasiloxane.

Useful silanes, disilanes, or alkoxysilanes include organic substituted silanes having the general formula:

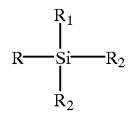

wherein R is a reactive group such as hydrogen, alkoxy, halogen, carboxy, amino, acetamide, trialkylsilyloxy $R_1$, $R_2$ and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length.

When used for the vapor phase disproportionation of toluene, the zeolite catalyst preferably comprises a bound aluminosilicate MFI-type zeolite having a silica to alumina mole ratio of from about 20 to about 200:1, preferably, 25:1 to about 120:1, and the crystals preferably have a mass mean diameter of from about 3 to 6 microns. The binder preferably is a MFI-type zeolite having an average particle size of less than about 0.1 micron and an alumina to silica mole ratio in excess of about 200:1.

Once the catalyst has been selectivated to the desired degree, reactor selectivation conditions are changed to disproportionation conditions. Disproportionation conditions include a temperature between about 375° C. and 550° C., more preferably between about 400° C. and 485° C., at a hydrogen to toluene mole ratio of from 0 to about 10, preferably between about 0.1 and 5 and more preferably from about 0.1 to 1, at a pressure between about 1 atmosphere and 100 atmospheres and utilizing WHSV of between about 0.5 and 50.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

The process of the present invention also finds particular application in a process for isomerizing one or more xylene isomers in a $C_8$ aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. Ethylbenzene in the feed is either removed from the stream or is converted during the process to xylenes or to benzene which are easily separated by distillation. The isomerate is blended with fresh feed and the combined stream is distilled to remove heavy and light by-products. The resultant $C_8$ aromatics stream is then recycled to repeat the cycle.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 0.1 to 30.0 moles of hydrogen per mole of alkylbenzene.

When use to isomerize feeds containing ethylbenzene, the zeolite catalyst will preferably contain at least one hydrogenation metal. Examples of such metals include the oxide, hydroxide, sulfide, or free metal (i.e., zero valent) forms of Group VIII metals (i.e., Pt, Pd, Ir, Rh, Os, Ru, Ni, Co, and Fe), Group IVB metals (i.e., Sn and Pb), Group VB metals (i.e., Sb and Bi), and Group VIIA metals (i.e., Mn, Tc, and Re). Noble metals (i.e., Pt, Pd, Ir, Rh, Os, and Ru) are preferred. Combinations of catalytic forms of noble or non-noble metals, such as combinations of Pt with Ni, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The amount of metal present in the zeolite catalyst will be an effective amount which will generally be from about 0.001 to about 10 percent by weight and, preferably 0.05 to 3.0 percent by weight. The amount will vary with the nature of the metal, less of the highly active metals, particularly platinum, being required than of the less active metals.

The process of the present invention is useful for cracking a naphtha feed, e.g., $C_{4+}$ naphtha feed, particularly a $C_4$-290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The process of the present invention is especially useful in the transalkylation of polyalkylaromatic hydrocarbons. Examples of suitable polyalkylaromatic hydrocarbons include di-, tri-, and tetra-alkyl aromatic hydrocarbons, such as diethylbenzene, triethylbenzene, diethylmethylbenzene (diethyl-toluene), diisopropyl-benzene, triisopropylbenzene, diisopropyltoluene, dibutylbenzene, and the like. Preferred polyalkylaromatic hydro-carbons are the dialkyl benzenes. Particularly preferred polyalkyl-aromatic hydrocarbons are diisopropylbenzene and diethylbenzene.

The feed used in the transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C. to maintain at least a partial liquid phase, and the pressure will be preferably in the range of about 50 psig to 1,000 psig, preferably 300 psig to 600 psig. The weight hourly space velocity will range from about 0.1 to 10.

The process of the present invention is also useful for converting aromatic compounds from paraffins. Example of suitable paraffins including aliphatic hydrocarbons containing 2 to 12 carbon atoms. The hydrocarbons may be straight chain, open or cyclic and may be saturated or unsaturated. Example of hydrocarbons include propane, propylene, n-butane, n-butenes, isobutane, isobutene, and straight- and branch-chain and cyclic pentanes, pentenes, hexanes, and hexenes.

The aromatization conditions include a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The zeolite catalyst used in the aromatization process preferably comprises large crystals of an intermediate pore size zeolite such a MFI type zeolite (example ZSM-5). The catalyst preferably contains gallium. Gallium may be incorporated into the during synthesis of the zeolite or it may be exchanged or impregnated or otherwise incorporated into the zeolite after synthesis. Preferably, 0.05 to 10, and most preferably 0.1 to 2.0 wt. % gallium is associated with the catalyst.

The following examples exemplify the process of the present invention.

EXAMPLE 1

Preparation of zeolite crystals with continuous stirring.

A synthesis mix was prepared as described for Catalyst A. The nix was placed in an autoclave and heated while stirring with a single blade turbine (0.8 M/second tip speed). In 6 hours a temperature of 150° C. was reached at autogenous pressure and stirring was continued at 150° C. for 48 hours during crystallization. After crystallization, a sample was taken. X-ray diffraction analysis showed the product was fully crystalline. Laser light scattering was used to determine the crystal size of the resulting crystals. The mass mean crystal diameter of the crystals was 2.76 microns and the amount of crystals less than 1 micron diameter was 7.2 percent.

EXAMPLE 2

Preparation of zeolite crystals without continuous stirring.

I. Preparation of Catalyst A

A sodium aluminate solution was prepared by dissolving alumina hydrate (201 parts by weight, 65% $Al_2O_3$ content) in a caustic solution comprising NaOH (369.1 parts by weight) and water (825 parts by weight) at 100° C. The solution was cooled and then added with vigorous stirring to a slurry containing colloidal silica (15400 parts by weight), tetrapropylammonium bromide (TPABr) (2457 parts by weight), water (16747 parts by weight), and 54 by weight MFI seeds to provide a synthesis mix. The mix was stirred until a homogeneous consistency was obtained. The molar composition of the mix, excluding seeds, was 80 $SiO_2$/1 $Al_2O_3$/3.6 $Na_2O$/7.2 TPABr/1168 $H_2O$. The mix (10 L) was placed in an autoclave and heated while stirring with a single blade turbine (0.8 M/sec tip speed). In 6 hours a temperature of 150° C. was reached at autogenous pressure. The heat up time between 140° C. and 150° C. was 20 min. The stirring was stopped and the mixture was allowed to crystallize without further agitation at 150° C. for 20 hours. After crystallization, a sample was taken. X-ray diffraction analysis showed the product was fully crystalline. Laser light scattering was used to determine the crystal size of the resulting crystals. The mass mean crystal diameter of the crystals was 3.67 microns and the amount of crystals less than 1 micron diameter was 4.5 percent. The acidic form of the zeolite was made by ion exchange using ammonium nitrate followed by calcination to remove ammonium and provide the acidic hydrogen form.

II. Preparation of Catalyst B

A synthesis mix was prepared as described in for Catalyst A except that the amount of seeds in the mix was 36 parts by weight. The mix (36 L) was placed in an autoclave and heated while stirring with a single blade turbine (0.8 M/sec tip speed). In 13.75 hours, a temperature of 140° C. was reached at autogenous pressure. The stirring was stopped and the mixture was allowed to crystallize without further agitation at 140° C. to 150° C. for 4.5 hours and then 20 hours at 150° C. for 24 hours. After crystallization, a sample was taken. X-ray diffraction analysis showed the product was fully crystalline. Laser light scattering was used to determine the crystal size of the resulting crystals. The mass mean crystal diameter of the crystals was 3.83 microns and the amount of crystals less than 1 micron diameter was 4.2 percent. The acidic form of the zeolite was made by ion exchange using ammonium nitrate followed by calcination to remove ammonium and provide the acidic hydrogen form.

EXAMPLE 3

Catalysts A and B was selectivated by feeding toluene across the catalyst under the conditions set forth in Table I below:

TABLE I

Selectivation Conditions

| | | Catalyst A | Catalyst B |
|---|---|---|---|
| Hours | | 218 | 192 |
| Temperature (° F.) | | 1100 | 1100 |
| Pressure (Psig) | | 225 | 225 |
| WHSV (#Feed/#Cat/Hr) | | 1.0 | 1.0 |
| $H_2$:Feed Toluene | Initial | 0.20:1 | 0.20:1 |
| Ratio (moles) | Final | 0.35:1 | 0.35:1 |
| Hydrocarbon Partial | Initial | 64.8 Psia | 64.8 Psia |
| Pressure | Final | 62.3 Psia | 62.3 Psia |

Following selectivation, Catalysts A and B were evaluated for the disproportionation of toluene under the test conditions shown in Table II below. On-oil catalyst performance for the Catalysts is shown in Table III.

TABLE II

On-Oil Conditions

| | Catalyst A | Catalyst B |
|---|---|---|
| Temperature (° F.) | 819 | 847 |
| Pressure (Psig) | 300 | 325 |
| WHSV (##Hr.) | 3.0 | 4.85 |
| $H_2$:Feed Toluene Ratio (moles) | 0.5 | 0.5 |
| Hydrocarbon Partial Pressure (Psig) | 197.6 | 213.3 |

TABLE III

On-Oil Catalyst Performance

| | Catalyst A | Catalyst B |
|---|---|---|
| Toluene Conversion (wt. %) | 30.1 | 30.6 |
| Paraxylene Selectivity PX/[PX + MX + OX]X100 | 92.8 | 90.3 |
| Benzene Yield (wt. %) | 13.3 | 13.7 |
| Xylene Yield (wt. %) | 15.0 | 14.8 |
| $C_5$−Yield (wt. %) | 0.5 | 0.9 |
| $C_9$+Yield (wt. %) | 0.8 | 0.9 |

The results show high xylenes production with high paraxylene selectivity (greater than 90%) is achievable with the hydrocarbon-conversion process of the present invention.

What is claimed is:

1. A process for converting hydrocarbons comprising contacting a hydrocarbon feedstream under hydrocarbon conversion conditions with a zeolite catalyst containing large crystals, said zeolite being made by a process comprising:

(a) heating an aqueous zeolite synthesis mixture comprising sources of trivalent metal oxide, silica, alkali metal cations, optionally from 0 to about 10 weight percent of seeds of zeolite, and optionally a directing agent, under agitation to a temperature equal to or less than the effective nucleation temperature of said aqueous zeolite reaction mixture; and, (b) heating said aqueous zeolite synthesis mixture in the absence of agitation at a temperature equal to or greater than the effective nucleation temperature of said aqueous zeolite reaction mixture.

2. The process recited in claim 1 wherein said zeolite is a large pore zeolite or an intermediate pore size zeolite.

3. The process recited in claim 2 wherein said trivalent metal is aluminum, gallium, boron, or iron.

4. The process recited in claim 3 wherein said zeolite has a structure type selected from the group consisting of LTL, MAZ, MEI, EMT, OFF, *BEA, MOR, MEL, MTW, MTT, MFI, FER, and TON.

5. The process recited in claim 4 wherein the hydrocarbon conversion process is selected from the group consisting of cracking of hydrocarbons, isomerization of alkyl aromatics, transalkylation of aromatics, disproportionation of alkylaromatics, alkylation of aromatics, reforming of naphtha to aromatics, conversion of paraffins and/or olefins to aromatics, and conversion of oxygenates to hydrocarbon products.

6. The process recited in claim 5 wherein said hydrocarbon conversion is carried out at conditions comprising a temperature of from about 100° C. to about 760° C., a pressure of about 0.1 atmosphere to about 100 atmospheres, a weight hourly space velocity of from about 0.08 hr$^{-1}$ to about 200 hr$^{-1}$.

7. The process recited in claim 6 wherein said zeolite is an aluminosilicate zeolite or a gallium silicate zeolite.

8. The process recited in claim 7 wherein said zeolite is an intermediate pore size zeolite.

9. The process recited in claim 8 wherein said large crystals have a mass mean diameter from about 3 to about 10 microns.

10. The process recited in claim 3 wherein said zeolite has a structure type selected from the group consisting of MFI, MEI, MTW, MTT, MFS, EUO, and TON.

11. The process recited in claim 10 wherein said zeolite crystals have a mass mean diameter in the range of from about 3 to about 6 microns.

12. The process recited in claim 10 wherein the temperature of step (a) results in a reduction of the mass mean crystal diameter of the zeolite crystals of less than 10%.

13. The process recited in claim 12 wherein said zeolite is a MFI to structure type.

14. The process recited in claim 13 wherein said zeolite is an aluminosilicate zeolite having a silica to alumina mole ratio of from about 10 to about 1000.

15. The process recited in claim 2 wherein said temperature of step (a) is no greater than 150° C.

16. The process recited in claim 15 wherein said temperature of step (b) is no greater than 150° C.

17. The process recited in claim 14 wherein said aqueous reaction mixture has the following composition in terms of mole ratios of oxides:

SiO$_2$:Al$_2$O$_3$ >50
H$_2$O:SiO$_2$ 10 to 100
OH$^-$:SiO$_2$ 0.01 to 0.5
R:SiO$_2$ 0.001 to 2.0 wherein R is a directing agent selected from a group consisting of nitrogen, sulfur, oxygen, and phosphorous containing inorganic and organic compounds.

18. The process recited in claim 2 wherein said zeolite catalyst further comprises a binder.

19. The process recited in claim 18 wherein said zeolite binder is zeolitic material.

20. The process recited in claim 13 wherein said process for making said zeolite comprises:

(a) forming an aqueous reaction mixture comprising sources of alumina, silica, alkali metal cations, optionally from 0 to 10 weight percent seed crystals; and, optionally a directing agent;

(b) heating the aqueous reaction mixture under agitation to a temperature no greater than the effective nucleation temperature of said aqueous reaction mixture; and, (c) heating the aqueous reaction mixture of step (b) in the absence of agitation to a temperature equal to or greater than the effective nucleation temperature of said aqueous reaction mixture and for sufficient time to result in the production of large zeolite crystals.

21. The process recited in claim 20, wherein said MFI structure type is an aluminosilicate zeolite having a silica to alumina mole ratio from about 50:1 to about 150:1.

22. A process for the disproportionation of toluene comprising contacting a hydrocarbon stream under toluene disproportionation conditions with an intermediate pore size zeolite catalyst containing large crystal zeolite, said large crystal zeolite made by a process comprising:

(a) heating an aqueous zeolite synthesis mixture comprising sources of trivalent metal oxide, silica, alkali metal cations, optionally from 0 to about 10 weight percent of seeds of zeolite, and optionally a directing agent under agitation to a temperature equal to or less than the effective nucleation temperature of said aqueous zeolite reaction mixture; and, (b) heating said aqueous zeolite synthesis mixture in the absence of agitation at a temperature equal to or greater than the effective nucleation temperature of said aqueous zeolite reaction mixture.

23. The process recited in claim 22 wherein said trivalent metal oxide is alumina, gallium oxide, boron oxide, or iron oxide.

24. The process recited in claim 23 wherein said zeolite has a structure type selected from the group consisting of MEL, MTW, MTT, MFI, EUO, MFS, and TON.

25. The process recited in claim 24 wherein said zeolite is an aluminosilicate zeolite.

26. The process recited in claim 25 wherein said zeolite catalyst is preselectivated.

27. The process recited in claim 26 wherein said zeolite catalyst is preselectivated by contacting the catalyst with a toluene stream at a temperature in the range of between 480° C. and 650° C. at a pressure within the range of from 1 to 100 atmospheres and a weight hourly space velocity in the range of 0.1 to 20, and wherein said toluene stream further contains hydrogen at a H$_2$/toluene ratio of 0 to about 2.

28. The process recited in claim 27 wherein said zeolite has a MFI structure.

29. The process recited in claim 28 wherein said toluene disproportionation conditions include contacting said toluene stream with said catalyst at a temperature in the range of between about 375° C. to 550° C., at a pressure in the range of from 1 to 100 atmospheres and at a weight hourly space velocity in the range of from about 0.5 to 50, and wherein said toluene stream further contains hydrogen at a H$_2$/toluene mole ratio in the range of 0 to about 10.

30. The process recited in claim 29 wherein said zeolite crystals have a mass mean diameter in the range of from about 3 to about 6 microns.

31. The process recited in claim 30 wherein the temperature of step (a) results in a reduction of the mass mean crystal diameter of the zeolite crystals of less than 10%.

32. The process recited in claim 29 wherein said MFI structure type zeolite is an aluminosilicate zeolite having a silica to alumina mole ratio of from about 10 to about 1000.

33. The process recited in claim 22 wherein said temperature of step (a) is no greater than 150° C.

34. The process recited in claim 33 wherein said temperature of step (b) is no greater than 150° C.

35. The process recited in claim 22 wherein said aqueous reaction mixture has the following composition in terms of mole ratios of oxides:

SiO$_2$:Al$_2$O$_3$ >50
H$_2$O:SiO$_2$ 10 to 100
OH$^-$:SiO$_2$ 0.01 to 0.5
R:SiO$_2$ 0.001 to 2.0 wherein R is a directing agent selected from a group consisting of nitrogen, sulfur, oxygen, and phosphorous containing inorganic and organic compounds.

36. A process recited in claim 29 wherein said process for making said zeolite comprises:

(a) forming an aqueous reaction mixture comprising sources of alumina, silica, alkali metal cations, optionally from 0 to about 10 weight percent seed crystals; and, optionally a directing agent;

(b) heating the aqueous reaction mixture under agitation to a temperature no greater than the effective nucleation temperature of said aqueous reaction mixture; and, (c) heating the aqueous reaction mixture of step (b) in the absence of agitation to a temperature equal to or greater than the effective nucleation temperature of said aqueous reaction mixture and for sufficient time to result in the production of large zeolite crystals.

37. The process recited in claim 36 wherein said aqueous reaction mixture of step (a) contains from about 0.05 ppm to about 0.1 percent by weight of seeds of zeolite.

38. The process recited in claim 37 wherein said temperature of step (b) is in the range of from about 130° C. to 150° C.

39. The process recited in claim 38 wherein said zeolite has a silica to alumina mole ratio from about 20:1 to about 200:1.

40. The process recited in claim 38 wherein said temperature of step (c) is in the range of from about 130° C. to 150° C.

41. The process recited in claim 40 wherein said crystals have a mean mass diameter of from about 3 to about 6 microns.

42. The process recited in claim 41 wherein said aqueous reaction mixture of step (c) is heated for up to 48 hours.

43. The process recited in claim 36 wherein the temperature of step (b) results in a reduction of the mass mean crystal diameter of the zeolite crystals of less than about 10%.

44. The process recited in claim 43 wherein said zeolite catalyst comprises a binder.

45. The process recited in claim 44 wherein said binder is zeolitic material.

46. The process recited in claim 45 wherein no more than 5% of the zeolite crystals on a mass basis have a diameter of less than 1 micron.

* * * * *